(12) United States Patent
Pavkov et al.

(10) Patent No.: US 6,527,151 B1
(45) Date of Patent: Mar. 4, 2003

(54) AEROSOL AIR FLOW CONTROL SYSTEM AND METHOD

(75) Inventors: Richard M. Pavkov, Plymouth, MI (US); Thomas A. Armer, Cupertino, CA (US); Nahed M. Mohsen, Farmington, MI (US)

(73) Assignee: Sheffield Pharmaceuticals, Inc., St. Louis, MO (US)

( * ) Notice: Subject to any disclaimer, the term of this patent is extended or adjusted under 35 U.S.C. 154(b) by 0 days.

(21) Appl. No.: 09/660,989

(22) Filed: Sep. 13, 2000

Related U.S. Application Data

(60) Provisional application No. 60/154,074, filed on Sep. 13, 1999.

(51) Int. Cl.[7] .............................................. A61M 11/00
(52) U.S. Cl. ................. 222/566; 222/564; 128/200.18; 128/200.19
(58) Field of Search ................................. 222/564, 566; 128/200.14, 200.18, 200.19, 200.21, 200.23

(56) References Cited

U.S. PATENT DOCUMENTS

| | | | | |
|---|---|---|---|---|
| 5,086,765 A | * | 2/1992 | Levine | 128/200.21 |
| 5,178,138 A | * | 1/1993 | Walstrom et al. | 128/200.23 |
| 5,617,844 A | * | 4/1997 | King | 128/200.18 |
| 5,954,047 A | * | 9/1999 | Armer et al. | 128/200.23 |
| 6,187,344 B1 | * | 2/2001 | Eljamal et al. | 424/489 |
| 6,230,704 B1 | * | 5/2001 | Durkin et al. | 128/200.22 |

FOREIGN PATENT DOCUMENTS

| | | |
|---|---|---|
| DE | 19728622 A | 1/1999 |
| GB | 1067486 A | 5/1967 |
| GB | 2152819 A | 8/1985 |
| JP | 57 107262 | 7/1982 |
| WO | WO 9748431 | 12/1997 |

* cited by examiner

Primary Examiner—J. Casimer Jacyna
(74) Attorney, Agent, or Firm—Fitzpatrick, Cella, Harper & Scinto

(57) ABSTRACT

Airflow in the exhaust piece of a fluid delivery device is forced through a series of gaps to achieve a split airflow. One component has a velocity and direction to impact on the source of the aerosol thus sweeping and entraining the aerosol off the aerosol generator into the directional air. The other airflow is used to protect the internal surfaces from aerosol deposition. The two air flows then recombine and are swept over a three dimensional surface or porous medium, used as an impaction or filtration site for determining the amount and particle size of the entrained aerosol at the exhaust exit.

21 Claims, 13 Drawing Sheets

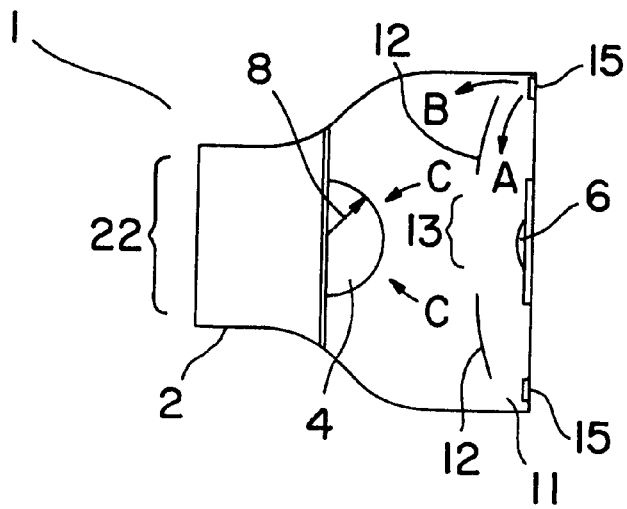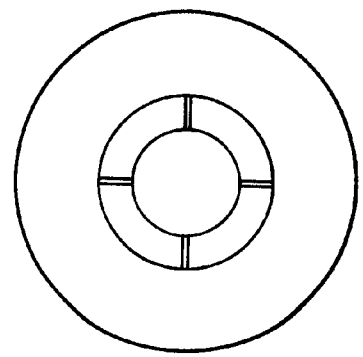
FIG. 1A  FIG. 1B
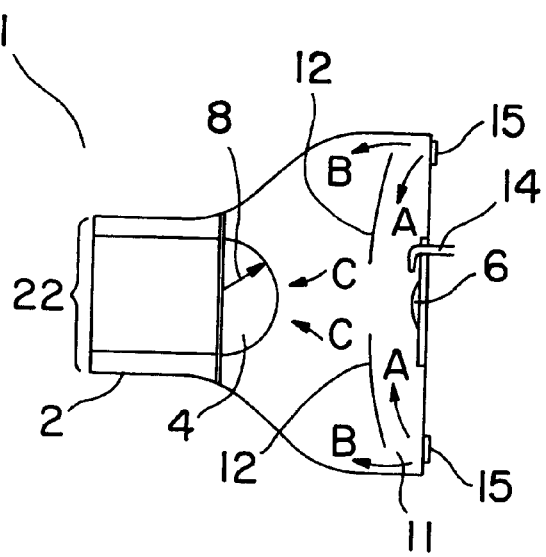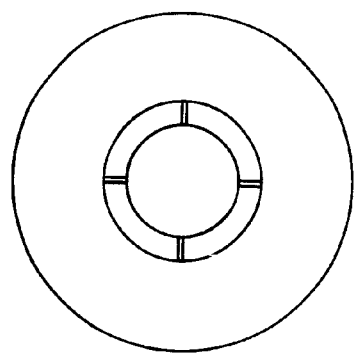
FIG. 2A  FIG. 2B

Effects of Inner Shroud Distance From Aerosol Generator

Legend:
- Respirable Dose (ug)
- Respirable Fraction (%)
- Efficiency (%)

FIG. 13

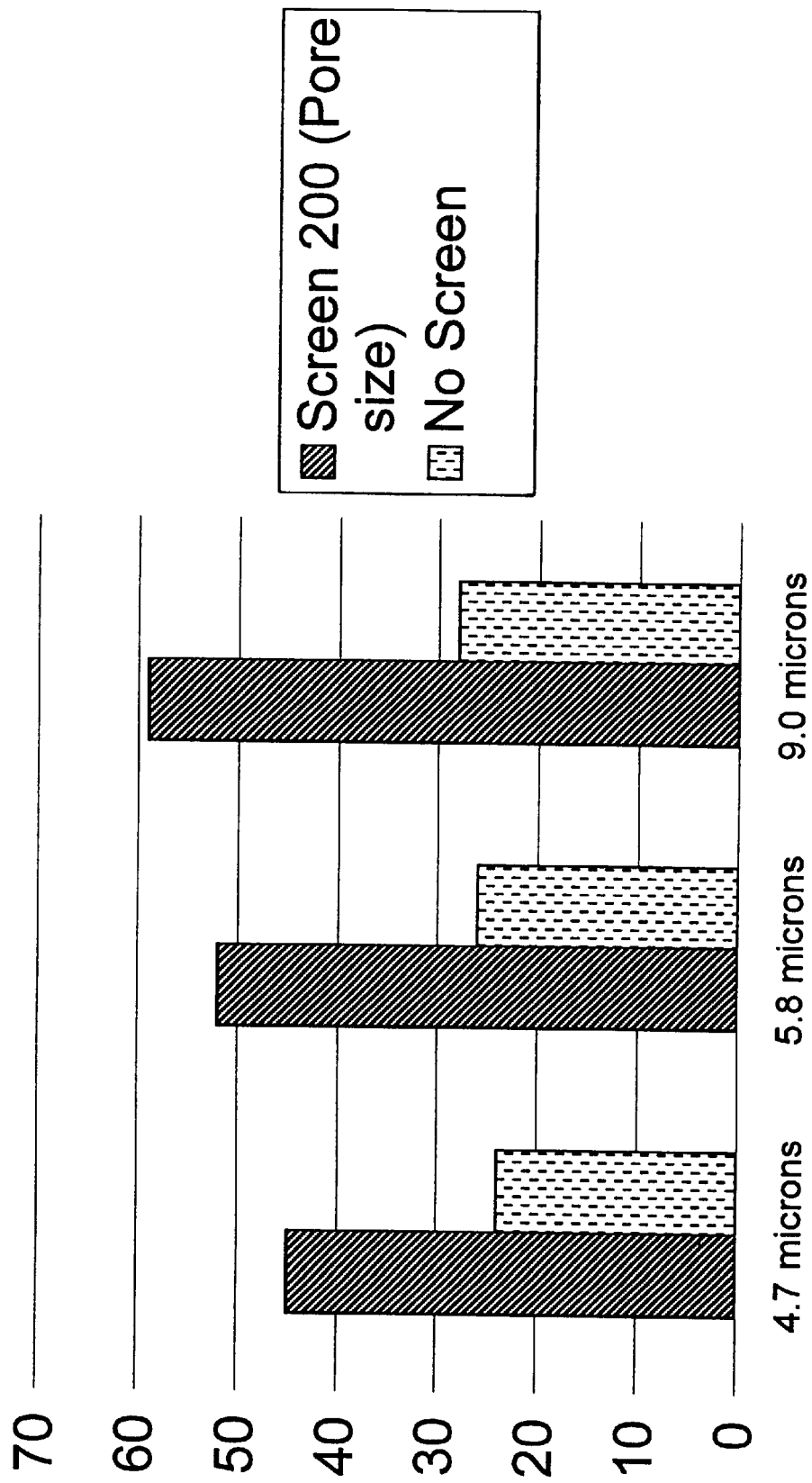

AEROSOL AIR FLOW CONTROL SYSTEM AND METHOD

This application claims benefit and incorporates by reference the entire disclosure of U.S. provisional patent application No. 60/154,074, filed Sep. 13, 1999.

FIELD OF THE INVENTION

The present invention relates to flow control and filtration methods and apparatuses relating to medical devices, drug delivery devices, food dispensing devices, aerosol generation devices and the like.

BACKGROUND OF THE INVENTION

Liquid atomizers are well known and come in several types, including aerosol, manual and ultrasonic. For example, there are aerosol atomizers for various applications, such as dispensing cosmetic and hygienic products (hair spray, deodorant, etc.) and cleaning solutions (disinfectants, air fresheners, etc.). Aerosol atomizers can also be used for dispensing medicaments although they have significant drawbacks when used for that purpose.

Ultrasonic atomizers include one type using a piezoelectric element to atomize a liquid medicament deposited thereon by manually moving a piston within a cylinder containing the medicament to be atomized. The piston forces the liquid from an outlet in the cylinder, which deposits it onto the piezoelectric atomizer, which in turn is activated as part of the manual medicament-dispensing operation.

These existing drug delivery systems, however, suffer from a number of disadvantages. One problem with existing drug delivery systems is poor delivery efficiency of the medication. It has been estimated that on average, with existing systems, only a small percentage of the medication dose which is dispensed from a fluid reservoir actually reaches the patient's lungs where it can achieve the intended result. A significant portion of the medication impacts and sticks to the inner surfaces of the device. This makes the drug delivery device less than optimal for delivering expensive medication.

Thus, there exists the need for an apparatus and/or method of improving the delivery efficiency of fluid delivery devices.

SUMMARY OF THE INVENTION

The present invention presents new and unique methods and apparatuses for creating a directional and entraining airflow over an aerosol generation surface and the internal walls of an exhaust (mouth) piece for a fluid dispensing device.

The present invention also presents methods and apparatuses for directing air flow through a filtration element to limit aerosol particle size. Thus, particle size distribution tailored to a particular size or range of sizes of particles.

The present invention is illustrated and described in conjunction with a nebulizer/inhalable drug delivery system. Such systems encompass dry powder generators, nebulizers (liquid generators), propellent generators, and the like.

Accordingly, in one aspect of the present invention, an exhaust member for an airflow control apparatus is presented. The airflow control apparatus includes a aerosol generation surface and a material dispensing member positioned adjacent thereto. The exhaust member includes a generally circular housing having an inner wall, a first end positioned adjacent the aerosol generation surface of the airflow control apparatus, an opening for exhausting a material entrained airflow out of the exhaust member, a plurality of inlets in communication with ambient air and an inner shroud positioned adjacent the inner wall establishing a gap therebetween. The shroud includes a central opening adjacent the aerosol generation surface.

In another aspect of the present invention, a method for delivering an aerosolized material from an exhaust ember of an airflow control apparatus includes the steps of discharging an amount of a material on an aerosol generation surface of the airflow control apparatus, where the aerosol generation surface is positioned adjacent a substantially closed end of the exhaust member of the apparatus. The method also includes the steps of aerosolizing the material via the aerosol generation surface, concurrently creating a first airflow for sweeping over the aerosol generation surface to entrain the aerosolized material, and a second airflow creating a layer of air between the first airflow and walls of the exhaust member. The method also includes the step of combining the first and the second airflows downstream from the aerosol generating surface.

In yet another aspect of the present invention, a method for delivering a dose of an aerosolized medicament from an exhaust member of a drug delivery device having an aerosol generation surface includes the steps of discharging a dose of a medicament on the aerosol generation surface of the drug delivery device, where the aerosol generation surface is positioned adjacent a substantially closed end of the exhaust member, aerosolizing the material via the aerosol generation surface, concurrently creating a first airflow for sweeping over the aerosol generation surface to entrain the aerosolized medicament, and a second airflow creating a layer of air between the first airflow and walls of the exhaust member, and combining the first and the second airflows downstream from the aerosol generating surface.

In yet another aspect of the present invention, a system for delivering an aerosolized material from an exhaust member of an airflow control apparatus includes discharging means for discharging an amount of a material, aerosolizing means for aerosolizing a material, where the discharging means discharges the material adjacent to the aerosolizing means, airflow generating means for concurrently creating a first airflow for sweeping over the aerosolizing means to entrain aerosolized material, and a second airflow creating a layer of air between the first airflow and walls of the exhaust member, and combining means for combining the first and the second airflows downstream from the aerosol generating surface.

A three-dimensional object may be used with the aspects of the present invention by placing it within a path of an entrained airflow prior to the airflow exiting through the opening. The three-dimensional objects may include a cylindrical shape, a circular, ellipsoidal or hemispherical shape, a planer shape, an interlocking mesh, and a cylindrical array.

The three-dimensional shape may also include a porous media. Such a porous media may establish a predetermined particle size based upon properties of the porous media. Such properties include at least one of a thickness of the media, a pore volume of the media, a pore size of the media and a hydrophillic/hydrophobic balance of the media.

The gap established between the shroud and the inner wall of the previous aspect may also be adjustable.

BRIEF DESCRIPTION OF THE DRAWINGS

FIG. 1A illustrates a side-schematic view of a mouthpiece for a flow control device according to the present invention.

FIG. 1B illustrates an end view of the mouthpiece for the flow control device according to the present invention.

FIG. 2A illustrates a side-schematic view of a mouthpiece for a flow control device according to the present invention.

FIG. 2B illustrates an end view of the mouthpiece for the flow control device according to the present invention.

FIG. 13 is a chart illustrating the effects of the inner shroud at a particular distance away from the aerosol generation surface of the flow control device according to the present invention.

FIG. 14 is a chart illustrating the efficiency versus particle size for the flow control device according to the present invention.

DESCRIPTION OF THE PREFERRED EMBODIMENTS

Figure 3A:
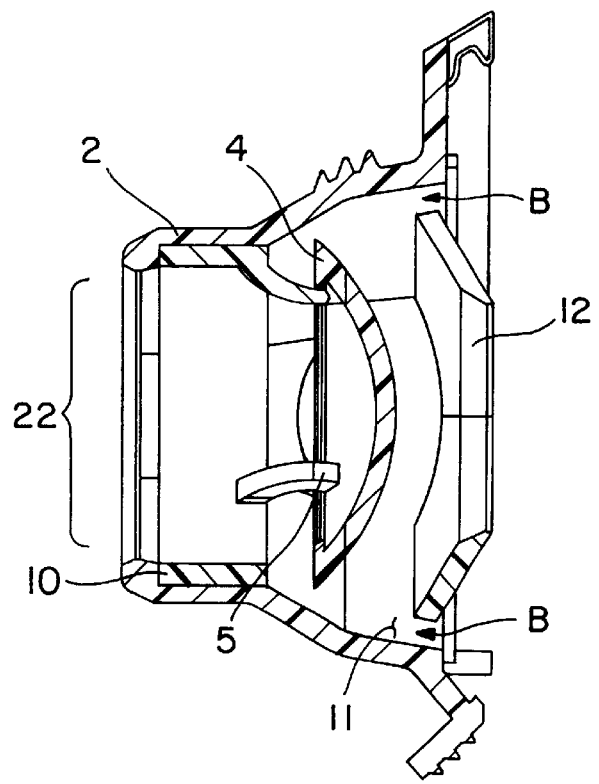
FIG. 3A illustrates a side-sectional view of an assembled mouthpiece for a flow control device according to the present invention.
Figure 3B:
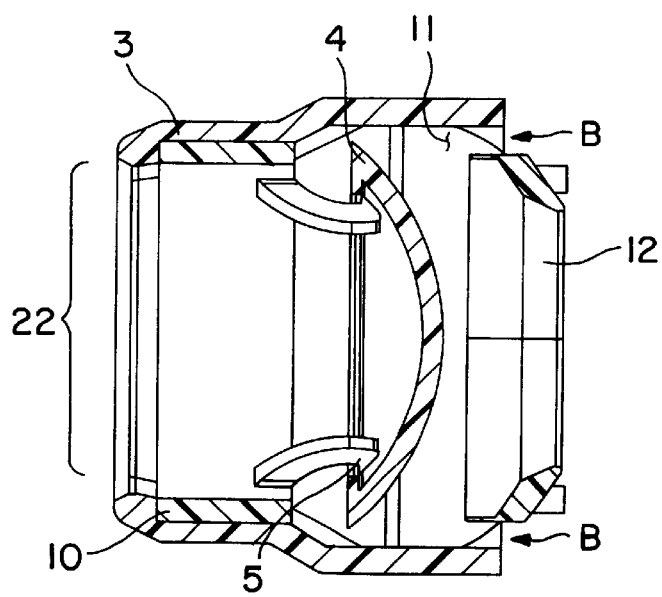
FIG. 3B illustrates a side-sectional view of an assembled mouthpiece for a flow control device according to the present invention.
Figure 4C:
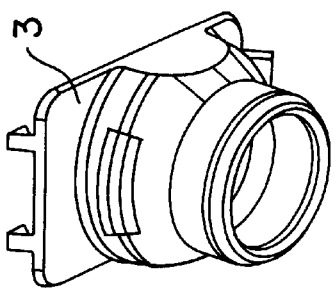
FIGS. 4A–F illustrate various views of an outer shroud for the mouthpiece for the flow control apparatus according to the present invention.
Figure 4F:
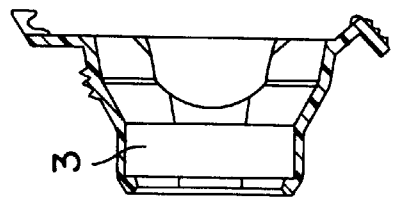
Figure 4B:
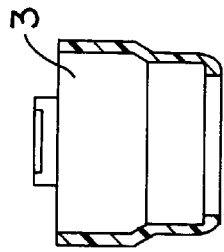
Figure 4E:
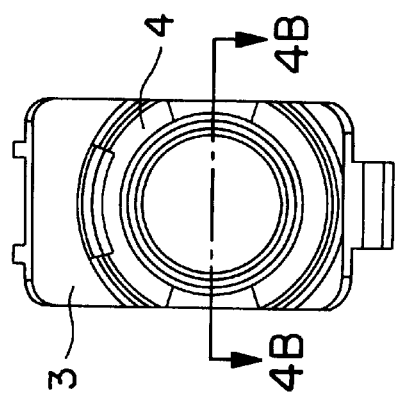
Figure 4A:
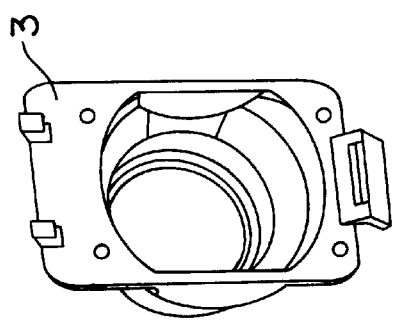
Figure 4D:
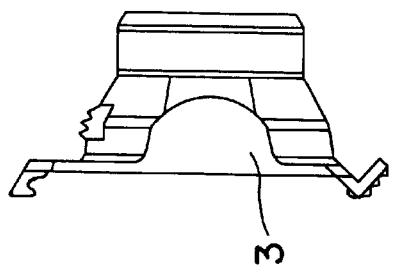
Figure 5C:
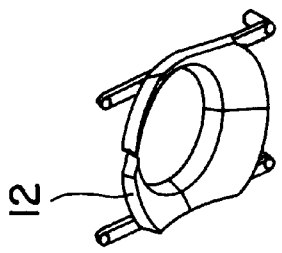
FIGS. 5A–F illustrate various views of an inner shroud for the mouthpiece for the flow control apparatus according to the present invention.
Figure 5F:
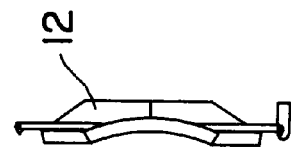
Figure 5B:
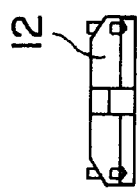
Figure 5E:
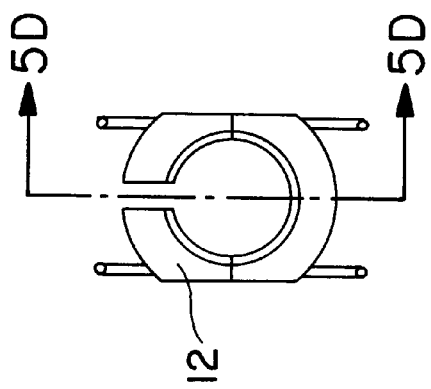
Figure 5A:
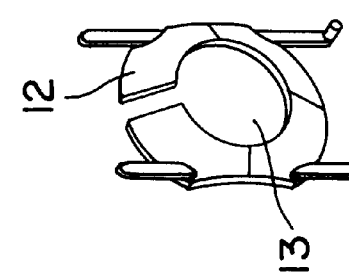
Figure 5D:
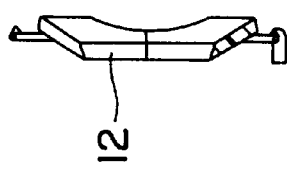
Figure 6C:
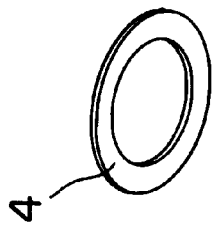
FIGS. 6A–F illustrate various views of a hemispherical insert for the mouthpiece for the flow control apparatus according to the present invention.
Figure 6F:
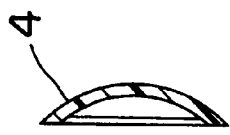
Figure 6B:
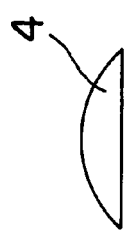
Figure 6E:
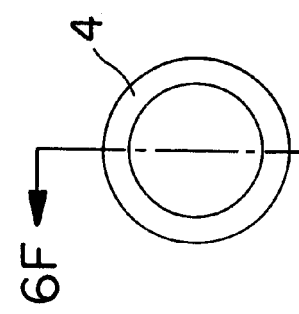
Figure 6A:
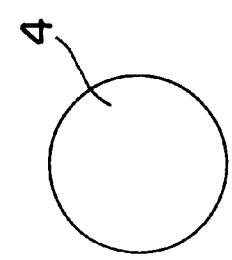
Figure 6D:
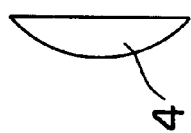
Figure 7C:
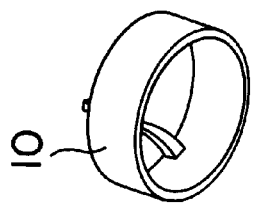
FIGS. 7A–F illustrate various views of a support ring for the mouthpiece for the flow control apparatus according to the present invention.
Figure 7F:
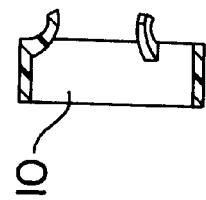
Figure 7B:
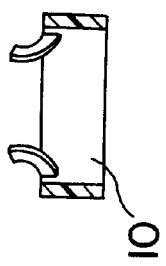
Figure 7E:
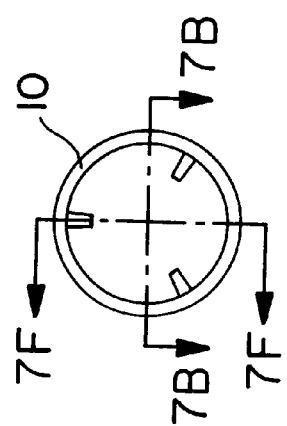
Figure 7A:
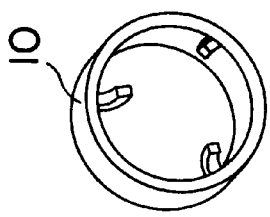
Figure 7D:
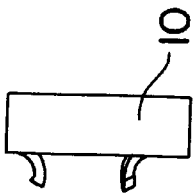
Figure 8:
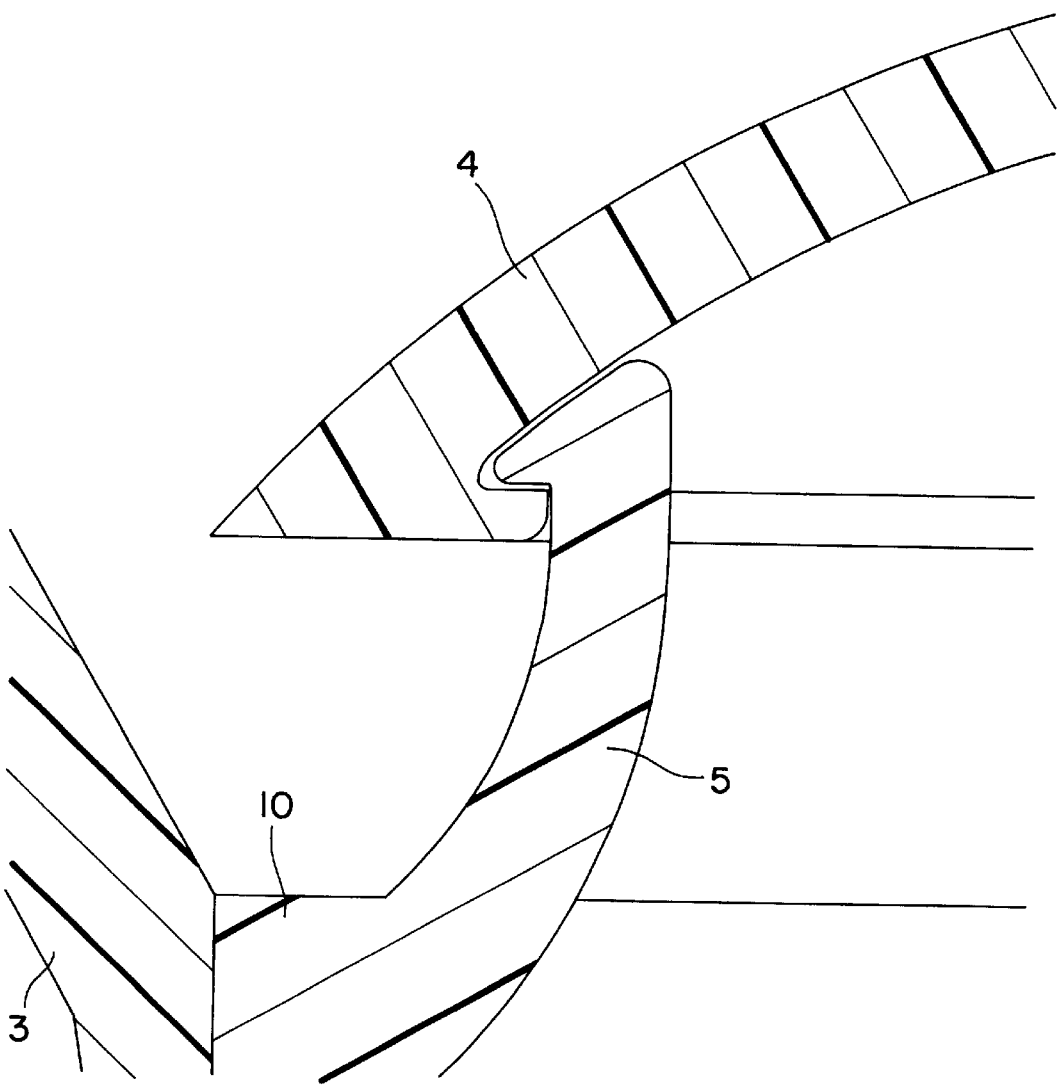
FIG. 8 illustrates the interlocking connection between the hemispherical insert and the support ring according to the present invention.

An exhaust or mouthpiece 1 for connection to an inhalable drug delivery device is presented. The assembled mouthpiece 1 includes a housing or outer shroud 2 having an exit or opening 22 positioned on an end of the housing located away from an aerosol generation surface 6 of a drug delivery device. The exhaust member also includes an inner shroud 12 having a center opening 13, an impacting, three-dimensional object 4 having a radius 8 and spaced away from the aerosol generating surface a distance 26 (see FIG. 9A). An impacting object support 10 supports the three-dimensional object within the housing.

As illustrated in the drawings, it is preferable that the alignment of the above elements should be indirect—i.e., it is preferably arranged such that there is no direct path (e.g., line of sight) between the center opening 13 and the outer perimeter of the three-dimensional impact object, to the diameter of the opening 22. The indirect path forces the aerosol particles to follow an airflow in order to exit the drug delivery device.

FIGS. 2A and B illustrate the use of an annular gap between the three-dimensional object 4, and the inner walls of the housing 2, adjacent the opening 22 at the exit of the mouthpiece.

The aerosol generation surface may include a piezoelectric horn which, upon activation, aerosolizes a material placed on its surface.

Figure 9A:
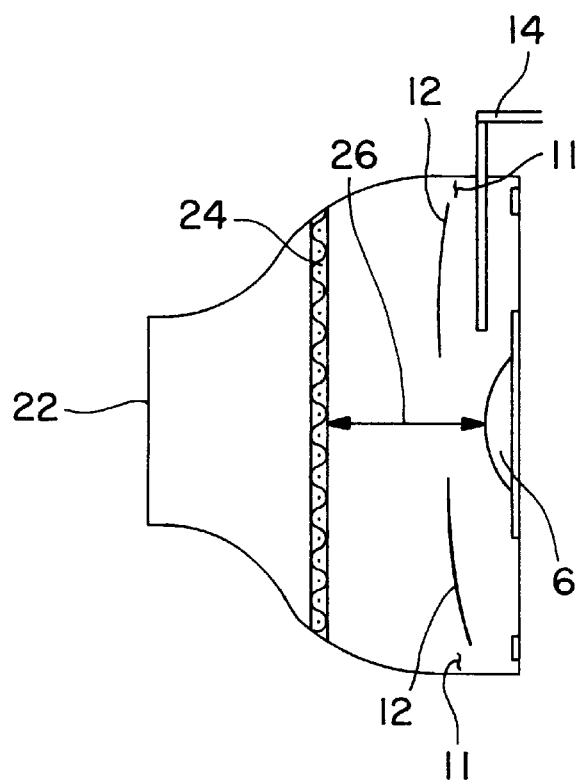
FIG. 9A illustrates a side-schematic view of a mouthpiece for a flow control device according to the present invention.
Figure 9B:
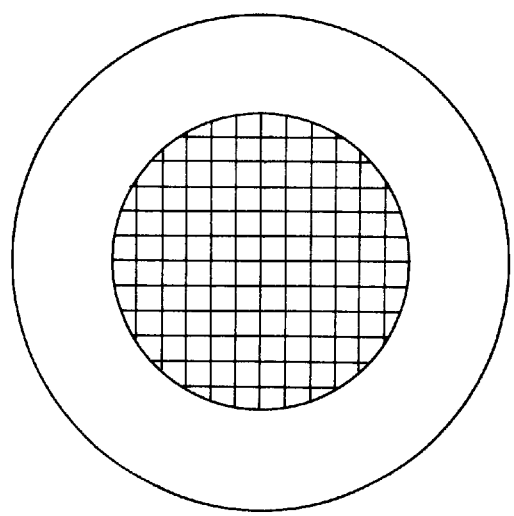
FIG. 9B illustrates an end view of the mouthpiece for the flow control device according to the present invention.

The three-dimensional object may be of any shape including a cylindrical shape, a hemispherical shape, a planer shape, an interlocking mesh (item 24 as shown in FIG. 9A), a cylindrical array and the like. A hemispherical shape is illustrated in the figures.

With regard to interlocking cylindrical meshes, the following may be used: PeCap® Polyester mesh 7-265/47, 7-440/40, 7-855/55 or equivalents thereto.

The three-dimensional object may also include a porous media such as a porous plastic. The porous media is selected having appropriate properties for establishing a predetermined exit particle size for a medicament airflow impacted upon its surface.

The support member 10 is illustrated as a support ring having an interlocking cam 5 for interlocking with an associated portion of the hemispherical impacting object. Such a portion may include a lip or an opening for receiving the cam. Conversely, the hemispherical object may include an interlocking tab for being received by a receiving portion within the mouthpiece.

Although the present invention is illustrated using a separate support member, impacting shape, and housing, one skilled in the art will appreciate that all three items may be manufactured in one piece using techniques, such as plastic injection molding, familiar to those in the art.

When a patient inhales through the device, airflow generated from a series of inlets 15 located at the back of the mouthpiece near the aerosol generation surface is directed towards the exit 22 of the mouthpiece. However, the airflow is first forced through a series of gaps 11 between the inner shroud and the internal walls of the mouthpiece forming a split airflow.

One portion of the airflow A (FIGS. 1–2) achieves a velocity and direction to sweep aerosolized particles generated off the aerosol generator surface, entraining them into the directional air. The other portion of the airflow B creates an air cushion between the aerosol entrained air flow and the internal walls of the mouthpiece, so that aerosol particles do not agglomerate on the internal walls of the mouthpiece.

Both air flows, aerosol generator sweeping and internal surface protecting, promote mixing and redirection of the air flow and entrained aerosol toward the mouthpiece exit as a combined airflow C. Prior to airflow C exiting the mouthpiece, it is swept over the three-dimensional and/or porous media in order to obtain a proper targeting effect for the aerosolized drug for a particular patient therapy.

The three-dimensional object and porous medium are used as an impaction or filtration site to limit the amount and particle size of the entrained aerosol at the exit of the mouthpiece. As the air flow passes over and through the object/porous media, a predetermined particle size is established for exiting the device.

Airflow may also be balanced between sweeping aerosolized particles off of the aerosol generator (airflow A) and protection of internal surfaces (airflow B). This is accomplished by adjusting the inlet gap 11 distances between the inner shroud and the internal walls of the mouthpiece, thus allowing for tuning of system.

The three dimensional impaction element according to the present invention functions as follows. A valve 14 retaining the fluid to be dispensed is positioned adjacent to an aerosolizer device 6. The valve 14 is opened dispensing a solution onto the horn which is simultaneously activated. The horn then aerosolizes the solution. At the same time the valve 14 opens to dispense solution onto the horn, a patient inhales and continues to inhale thereafter through the mouthpiece of the inhaler device. Ambient air enters a plurality of inlets 15 positioned adjacent the end of the mouthpiece near the aerosol generation surface. The resulting air flow is split into two components: one directed at the aerosol generator (A) and the other for creating an air cushion for protection of the internal walls of the mouthpiece (B). The two components of the airflow combine downstream from the aerosol generator to form airflow C. Thereafter, the combined air flow is forced over a three dimensional object 4.

Particle size may be tailored to a specific target when using the porous media. Such porous media may include PeCap® Polyester 7-200/44 and Nitex® Nylon 3-20/14.

Figure 10:
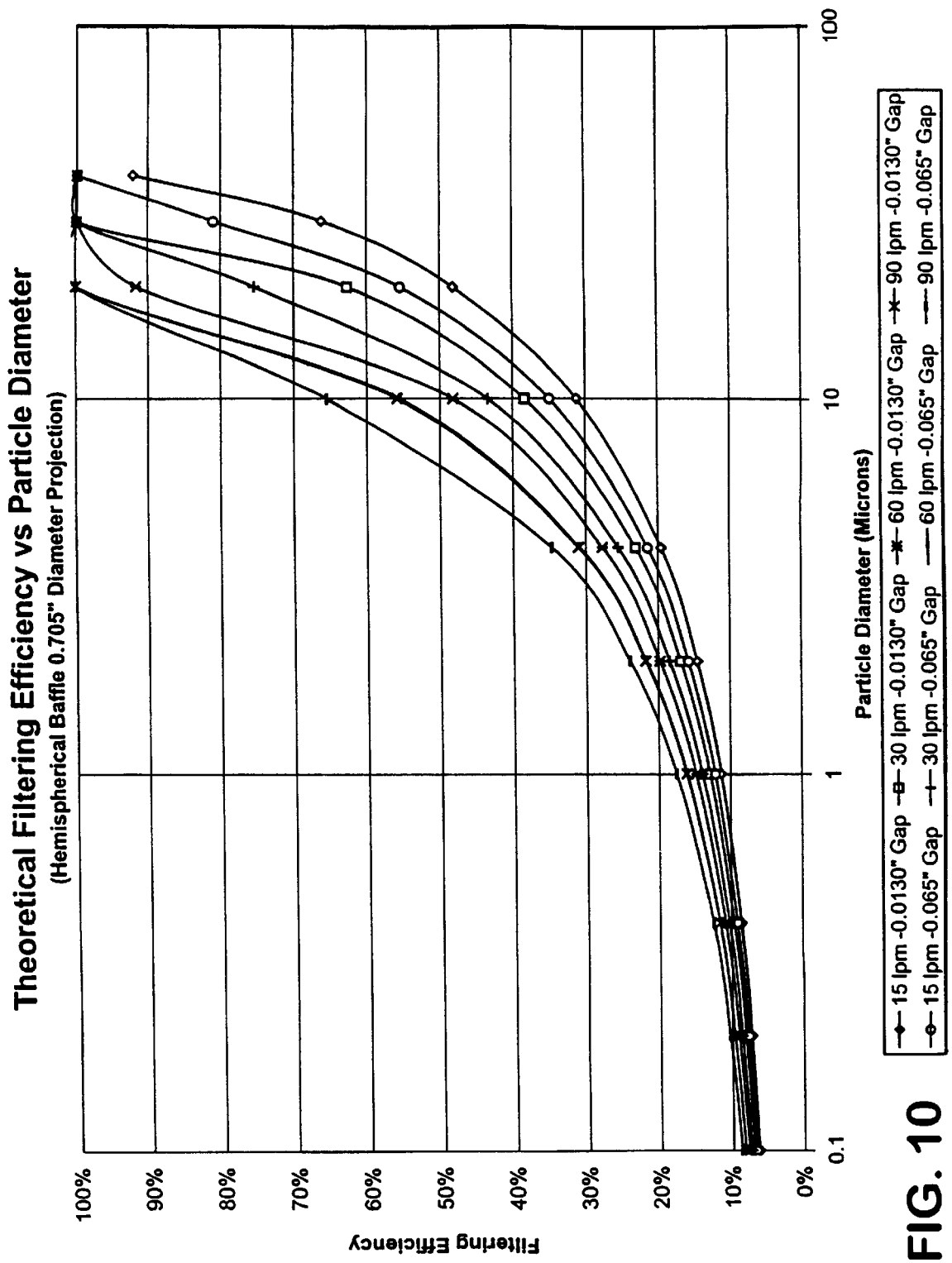
FIG. 10 is a graph illustrating the filtering efficiency versus particle diameter for a mouthpiece according to the present invention.
Figure 11:
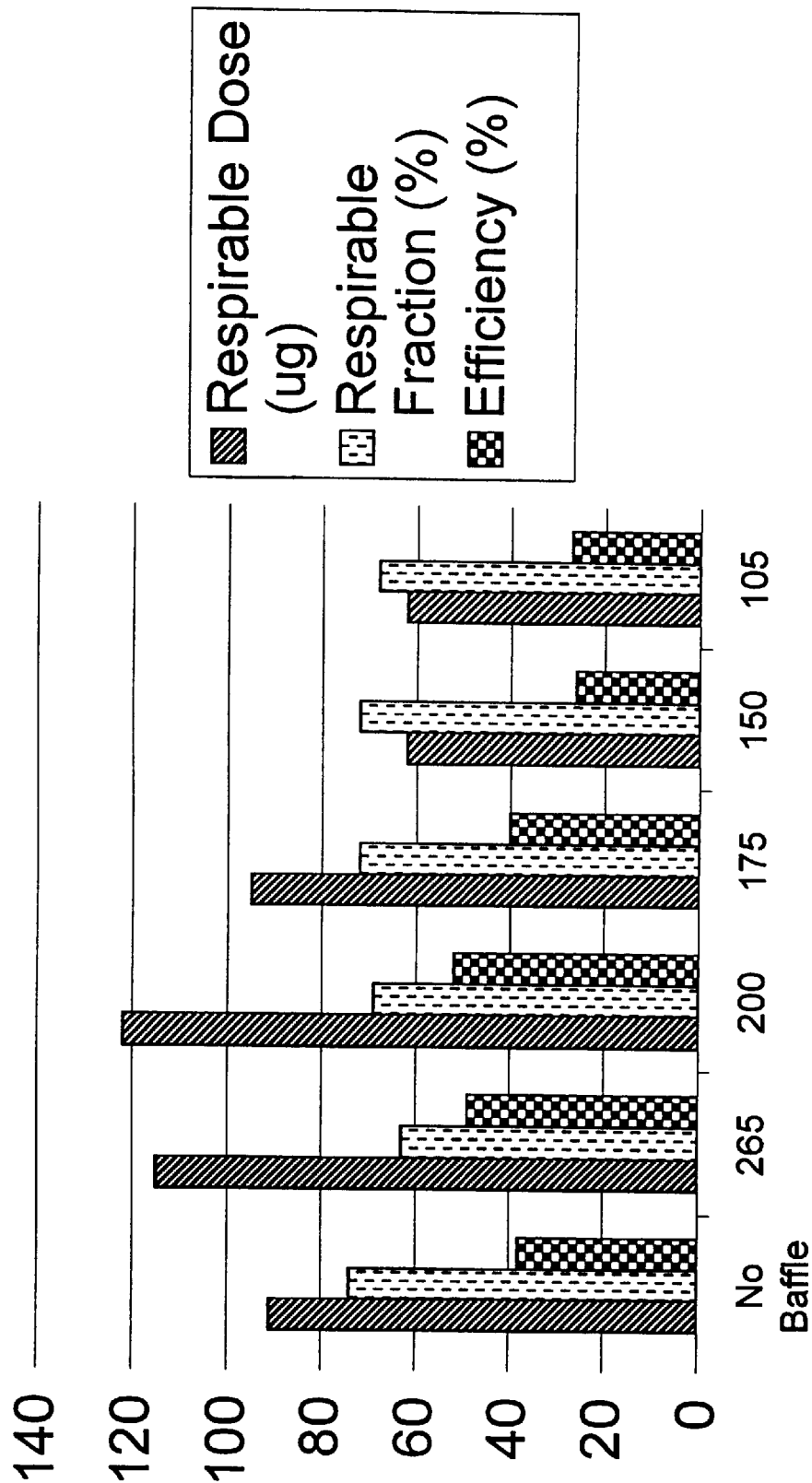
FIG. 11 is a chart illustrating the performance of the flow control device according to the present invention using a cylindrical mesh as an impacting object.
Figure 12:
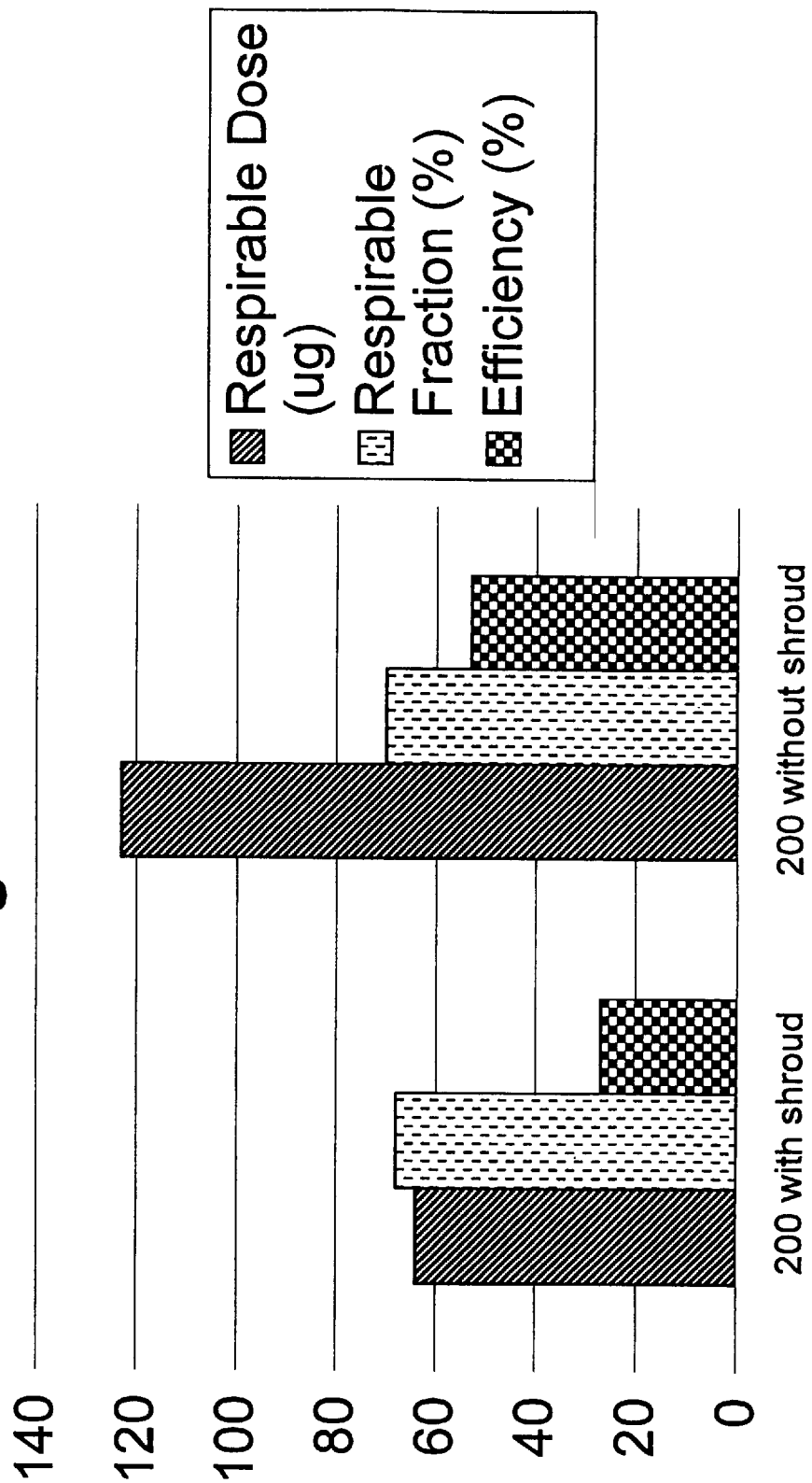
FIG. 12 is a chart illustrating the effects of using a cylindrical mesh with and without an inner shroud for the flow control device according to the present invention.

The remainder of the figures illustrate the improvements in different efficiencies for a drug delivery apparatus according to the present invention. Specifically:

FIG. 10 illustrates the filtering efficiency versus particle diameter;

FIG. 11 illustrates the performance of the exhaust member utilizing a cylindrical mesh as an impacting object;

FIG. 12 illustrates the effects of using a cylindrical mesh with and without the inner shroud;

FIG. 13 illustrates the effects of the inner shroud at a particular distance away from the aerosol generation surface.

FIG. 14 is a chart illustrating the efficiency versus particle size for the flow control device according to the present invention.

Other variations and modifications of this invention will be apparent to those skilled in this art after careful study of this application. This invention is not to be limited except as set forth in the following claims.

What is claimed is:

1. An exhaust member for an airflow control apparatus, said apparatus including a aerosol generation surface and a material dispensing member positioned adjacent thereto, said exhaust member comprising:
   a generally circular housing having an inner wall;
   a first end positioned adjacent said aerosol generation surface of said airflow control apparatus;
   an opening for exhausting a material entrained airflow out of said exhaust member;
   a plurality of inlets in communication with ambient air; and
   an inner shroud positioned adjacent said inner wall establishing a gap therebetween, said shroud including a central opening adjacent to said aerosol generation surface.

2. The exhaust member according to claim 1, wherein said inner shroud splits an airflow created by applying a pressure drop across said opening of said exhaust member, said airflow created from ambient air entering said inlets as a result of said pressure drop.

3. The exhaust member according to claim 2, wherein said split airflow comprises a first airflow having a velocity and direction for entraining aerosolized particles from said aerosol generation surface and a second airflow having a velocity and direction for creating a layer of air between said first airflow and said inner walls of said housing.

4. The exhaust member according to claim 3, wherein said airflows form a combined airflow downstream from said aerosol generation surface.

5. The exhaust member according to claim 4, further comprising a three-dimensional object placed within a path of said combined airflow.

6. The exhaust member according to claim 5, wherein said three-dimensional object comprises at least one of a cylindrical shape, a circular shape, a ellipsoidal shape, a hemispherical shape, a planer shape, an interlocking mesh, and a cylindrical array.

7. The exhaust member according to claim 5, wherein said three-dimensional object comprises an impacting hemisphere supported within said shroud, said hemisphere having a convex side facing said aerosol generation surface, wherein said first entrained airflow impacts upon said hemisphere prior to exiting through said opening.

8. The exhaust member of claim 3, further comprising a porous media placed within a path of said first entrained airflow prior to said airflow exiting through said opening.

9. The exhaust member according to claim 8, wherein said porous media establishes a predetermined particle size based upon properties of said porous media, said properties including at least one of a thickness of said media, a pore volume of said media, a pore size of said media and a hydrophillic/hydrophobic balance of said media.

10. The exhaust member according to claim 1, wherein said gap between said shroud and said inner wall is adjustable.

11. The exhaust member according to claim 1, wherein said dispensing member comprises a valve.

12. The exhaust member according to claim 1, wherein said aerosolized generation surface comprises a piezoelectric horn.

13. A method for delivering an aerosolized material from an exhaust member of an airflow control apparatus, said method comprising the steps of:
   discharging an amount of a material on an aerosol generation surface of said airflow control apparatus, said aerosol generation surface positioned adjacent a substantially closed end of said exhaust member of said apparatus;
   aerosolizing said material via said aerosol generation surface; and
   concurrently applying a pressure drop across an opening of said exhaust member to create an airflow from ambient air entering from one or more inlets;
   splitting said airflow to create first and second airflows by use of an inner shroud located within the exhaust member; and
   combining said first and said second airflows downstream from said aerosol generating surface.

14. The method according to claim 13, further comprising the step of directing said combined airflow against a three-dimensional element.

15. The method according to claim 14, wherein said three-dimensional element comprises any one of a cylindrical shape, a circular shape, an ellipsoidal shape, a hemispherical shape, a planer shape, an interlocking mesh, and a cylindrical array.

16. The method according to claim 14, wherein said three-dimensional object comprises an impacting hemisphere supported within a shroud positioned within said exhaust member, said hemisphere having a convex side facing said aerosol generation surface, wherein said fourth airflow impacts upon said hemisphere prior to exiting through said opening.

17. The method according to claim 13, further comprising the step of directing said combined airflow against a porous medium.

18. The method according to claim 17, wherein said porous media establishes a predetermined particle size based upon properties of said porous media, said properties including at least one of a thickness of said media, a pore volume of said media, a pore size of said media and a hydrophillic/hydrophobic balance of said media.

19. The method according to claim 13, wherein said aerosol generating surface comprises a piezoelectric horn.

20. A method for delivering a dose of an aerosolized medicament from an exhaust member of a drug delivery device, said method comprising the steps of:

discharging a dose of a medicament on an aerosol generation surface of said drug delivery device, said aerosol generation surface positioned adjacent a substantially closed end of said exhaust member of said apparatus;

aerosolizing said material via said aerosol generation surface;

concurrently applying a pressure drop across an opening of said exhaust member to create an airflow from ambient air entering from one or more inlets;

splitting said airflow to create first and second airflows by use of an inner shroud located within the exhaust member; and combining said first and said second airflows downstream from said aerosol generating surface.

21. A system for delivering an aerosolized material from an exhaust member of an airflow control apparatus, said apparatus including an aerosol generating surface, said system comprising:

discharging means for discharging an amount of a material;

aerosolizing means for aerosolizing a material, said discharging means discharging said material adjacent to said aerosolizing means;

airflow generating means for concurrently applying a pressure drop across an opening of said exhaust member to create an airflow from ambient air entering from one or more inlets;

splitting said airflow to create first and second airflows by use of an inner shroud located within the exhaust member; and combining means for combining said first and said second airflows downstream from said aerosol generating surface.

* * * * *